May 26, 1964 J. LUISI Plant Pat. 2,406
PLUM TREE
Filed Nov. 15, 1962
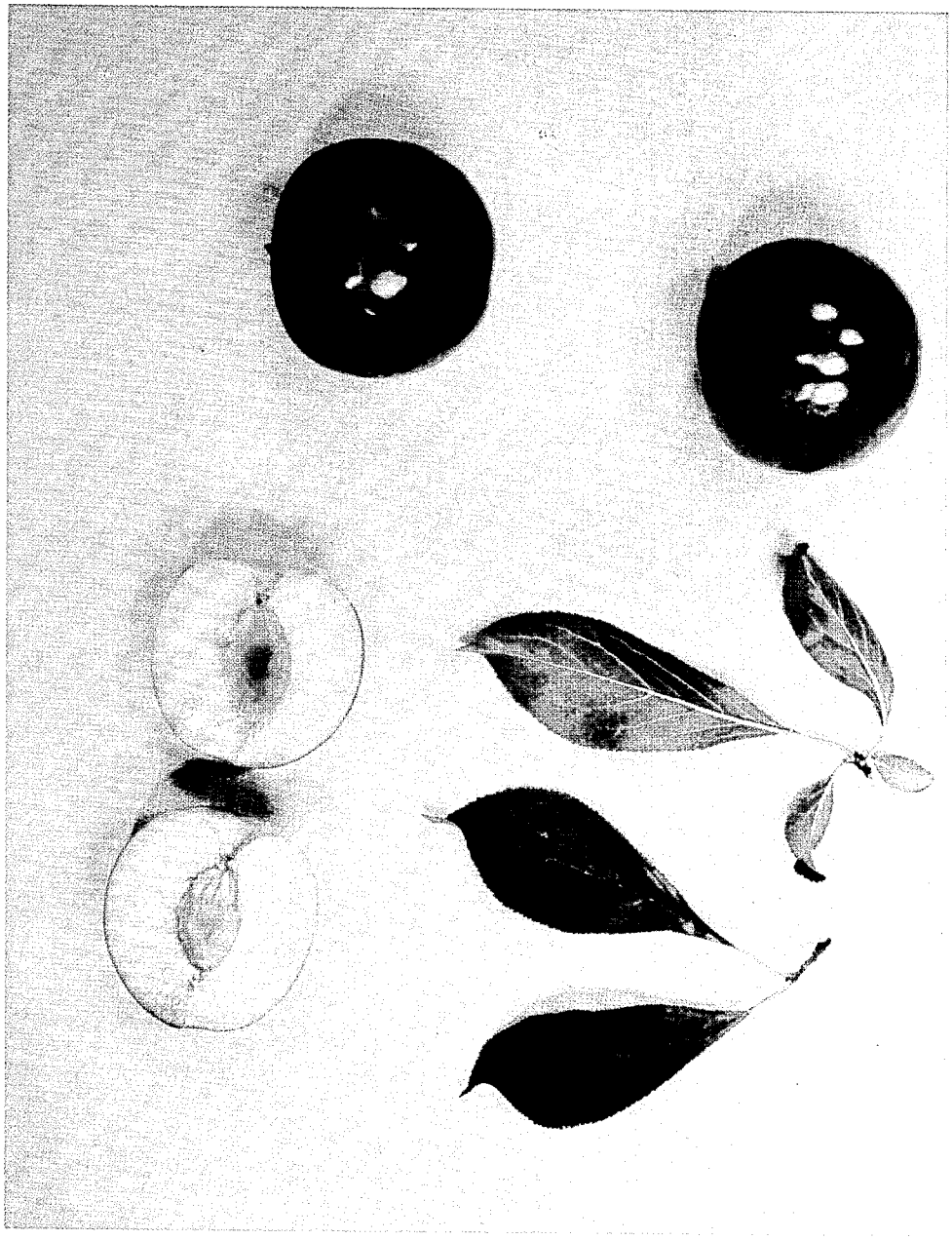
Inventor.
John Luisi
By: Robb & Robb
Attorneys United States Patent Office Plant Pat. 2,406
Patented May 26, 1964

2,406
PLUM TREE

John Luisi, 1609 W. Tulare Ave., Visalia, Calif.

Filed Nov. 15, 1962, Ser. No. 238,067
1 Claim. (Cl. Pit.—38)

The present invention relates to a new and distinct variety of plum tree which orignated as a sport of the variety known as "Santa Rosa" (unpatented), said sport having been discovered by me in my cultivated orchard located in the Taurusa area, northeast of Visalia, in Tulare County, California.

During the course of my cultivation and care of my orchard, aforementioned, my attention was attracted to one particular "Santa Rosa" plum tree at the end of a row of a block of regular "Santa Rosa" trees. A limb of this particular tree bore fruit which appeared to be substantially different from the fruit on the remainder of the tree and on the trees adjacent the same, and I thereupon took steps to carefully preserve the sport to see what would develop therefrom. During the following pruning season, the sport limb was left intact and was allowed to bear fruit for several years, after which grafts thereof were made onto other trees and understocks, and still later, the sport was further asexually reproduced more extensively by budding, all as performed in the vicinity of Visalia, California. As the result of the foregoing observations and asexual reproductions, which have been carried out over a period of nearly ten years, I am convinced that the new sport is definitely distinguished from the parent variety "Santa Rosa," as well as all other varieties of which I am aware, as evidenced by the following unique combination of characteristics which are outstanding therein:

(1) A blooming habit ranging from 2 or 3 days to at least a week earlier than "Santa Rosa";

(2) Larger and more globular fruit;

(3) A maturity period ranging from 4 or 5 days to at least a week earlier than "Santa Rosa," said fruit maturing relatively uniformly and needing only one or two pickings to completely strip the tree;

(4) An attractive and more uniform red color of the fruit skin which becomes fully high colored over the entire surface while the fruit is still firm, thus permitting the fruit to hang longer on the tree without having to be picked as soon as full color develops, as in the case of many varieties, so as to attain larger size and maturity such that complete stripping of the tree can be achieved in one or two pickings;

(5) A relatively dry fruit flesh which is not as tart next to the stone as the fruit flesh of "Santa Rosa," and is lighter and more amber in color;

(6) Good flavor; and (7) Fruit has better storage and shipping qualities than the fruit of "Santa Rosa," with less breakdown of the fruit during storage or as the result of rough handling during shipment.

In comparison with the variety known as "Gar-Rosa" (Plant Patent No. 1,518), the fruit of my new variety measures slightly larger on the average, the color of the flesh is substantially lighter and more amber, and the color of the skin is brighter and more attractive, amongst other differences.

The accompanying drawing shows typical specimens of the foliage and fruit of my new variety as depicted in color as nearly true as it is reasonably possible to make the same in a color illustration of this character, with both the upper and lower surfaces of a typical specimen leaf being illustrated, and the fruit specimens being shown in both elevation and cross section, one of the sectional views showing the pit cavity and the other sectional view exposing the pit.

The following is a detailed description of my new variety, with color terminology in accordance with the Nickerson Color Fan, published by Munsell Color Company, Inc., of Baltimore, Maryland, except where general color terms of ordinary dictionary significance are obvious:

Parentage: Sport of "Santa Rosa."

Propagation: Holds its distinguishing characteristics through succeeding propagations by both grafting and budding.

Locality where grown and observed: Near Visalia, Tulare County, California.

Dates of first and last pickings: Varies somewhat from year to year according to seasonal conditions, but usually ranging between the first and third weeks of June.

Tree: Large; vigorous; upright; dense; vase formed; hardy; good productivity; regular bearer.

*Trunk.*—Medium stockiness; medium smoothness.

*Branches.*—Medium stockiness. Color—dull brown.

*Leaves.*—Length—from about 1¼ inches to 3¾ inches. Width—from about ⅝ inch to 1½ inches. Size—medium. Shape—from ovate to obovate; acuminate; abruptly pointed; medium thickness; smooth. Margin—crenate; coarsely serrate. Petiole—medium length; medium thickness. Glands—usually two on average and located on margin of leaf near petiole; alternate; small; globose; color—brown. Color: upper side—near Moderate Olive Green, Plate 7.5GY 4/4; under side—near Moderate Yellow Green, Plate 7.5GY 5/7.

*Flower buds.*—Generally similar to those of "Santa Rosa"; half hardy; large; medium length; obtuse; plump; free. Dates of first and full bloom—ranges from 2 or 3 days to a week earlier than "Santa Rosa"; medium earliness as compared with other varieties. Size—medium. Color—white.

Fruit:

*Maturity.*—Ranges from 4 or 5 days to a week earlier than the fruit of "Santa Rosa" in same firm to hard stage.

*Size.*—Relatively uniform; relative large. Axial diameter—from about 2 inches to 2 7/16 inches. Transverse diameter in suture plane—from about 2 inches to 2½ inches. Diameter at right angles to suture plane—from about 1 15/16 inches to 2⅝ inches.

*Form.*—From globose to slightly ovoid; uniform.

*Suture.*—An inconspicuous shallow line; has slight depression beyond pistil point near stylar scar; suture line is darker than remainder of fruit.

*Ventral surface.*—Slightly rounded. Lips—nearly equal.

*Cavity.*—Flaring; elongated in suture plane. Depth—from about 5/16 inch to ⅜ inch. Breadth—from about 7/16 inch to ½ inch. Markings—none.

*Base.*—From rounded to slightly truncate.

*Apex.*—From rounded to slightly depressed. Pistil point—flat.

*Stem.*—Length ranges from about ½ inch to ⅝ inch; medium thickness; glabrous; medium adherence to stone.

*Skin.*—Thick; tough; tenacious to flesh; no tendency to crack during dry seasons. Down—wanting. Bloom—moderate. Color—near Moderate Red, Plate 2.5R 4/10, with buff colored dots well distributed throughout; Red color darkens as fruit fully ripens.

*Flesh.*—Color—from near white to near Brilliant Yellow, Plate 2.5Y 9/9, with Deep Purplish Red, Plate 10RP 3/10 tinge next to skin when mature and more extensively spread in flesh at apex end of fruit. Surface of pit cavity: color—amber.

Juice—moderate; rich. Texture—firm; crisp. Fibers—few; fine; tender. Ripens—evenly. Flavor—good; sweet. Aroma—distinct. Eating quality—excellent.

Stone: Cling; adheres to flesh over entire surface.

*Size.*—Medium. Length—from about 13/16 inch to 1 inch. Breadth—about ½ inch. Thickness—from about 9/16 inch to 11/16 inch.

*Form.*—Ovoid.

*Base.*—Straight; narrow hilum; dull point at apex.

*Sides.*—Equal.

*Surface.*—Furrowed slightly near ventral edge.

*Ridges.*—Rounded.

*Pits.*—Wanting.

*Dorsal edge.*—Narrow.

*Tendency to split.*—Slight.

*Color.*—Generally amber and near Moderate Orange Yellow, Plate 10YR 8/10.

Use: Market; dessert.

Keeping quality: Very good; has kept very well for periods of several months in cold storage, with little tendency of fruit to breakdown.

Shipping quality: Very good; firm flesh enables fruit to withstand rough handling during packing and shipping.

I claim:

A new and distinct variety of plum tree, substantially as herein shown and described, characterized particularly as to novelty by the unique combination of a blooming habit ranging from two or three days to a week earlier than the variety "Santa Rosa" (unpatented), fruit which averages larger in size and of more globular form than the fruit of "Santa Rosa," an earlier and more uniform maturity of the fruit ranging from four or five days to a week earlier than the fruit of "Santa Rosa," an attractive and uniform Red color of the fruit skin, with the color extending over the entire surface and becoming fully high colored while the fruit is still firm, relatively dry flesh and a lighter and more Amber color thereof than the flesh of "Santa Rosa" fruit, with the flesh being less tart next to the stone, a very good fruit flavor, and very good storage and shipping qualities.

No references cited.